United States Patent
Alba et al.

(10) Patent No.: US 6,233,046 B1
(45) Date of Patent: May 15, 2001

(54) METHOD OF MEASURING THE THICKNESS OF A LAYER OF SILICON DAMAGED BY PLASMA ETCHING

(75) Inventors: Simone Alba; Claudio Savoia, both of Milan; Enrico Bellandi, Domodossola-Verbania; Francesca Canali, Saronna-Varese, all of (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 0 days.

(21) Appl. No.: 09/343,207

(22) Filed: Jun. 29, 1999

(30) Foreign Application Priority Data

Jun. 30, 1998 (IT) ................................. MI98A1504

(51) Int. Cl.$^7$ ................................. G01B 11/06; G01J 4/04
(52) U.S. Cl. ................................. 356/38; 356/369
(58) Field of Search ................................. 356/369, 351, 356/382

(56) References Cited

U.S. PATENT DOCUMENTS

| | | | |
|---|---|---|---|
| 5,091,320 | * | 2/1992 | Aspnes et al. ................... 356/369 |
| 5,665,214 | * | 9/1997 | Iturralde ........................... 356/369 |
| 5,835,221 | * | 11/1998 | Lee et al. .......................... 356/369 |

* cited by examiner

*Primary Examiner*—Richard A. Rosenberger
(74) *Attorney, Agent, or Firm*—Theodore E. Galanthay; E. Russell Tarleton; SEED IP Law Group PLLC

(57) ABSTRACT

The method described comprises the following steps:

measuring, with a spectroscopic ellipsometer, the values of two quantities which are dependent on the thickness of the altered silicon layer and of a thin layer of silicon dioxide grown thereon with variations in the wavelength of the light of the measurement beam of the ellipsometer, obtaining from these measured values respective experimental curves representing the two quantities as functions of the wavelength, calculating the theoretical curves of the two quantities as functions of the wavelength considering the refractive indices and absorption coefficients of silicon dioxide and of the altered silicon as known parameters and the thickness of the altered silicon layer and the thickness of the thin silicon dioxide layer as unknowns, comparing the theoretical curves with the respective experimental curves in order to determine for which values of the unknowns the curves under comparison approximate to one another best, and extracting from the values determined the value which relates to the thickness of the altered silicon layer.

The time required for the measurements and calculations is a few minutes.

7 Claims, 2 Drawing Sheets

METHOD OF MEASURING THE THICKNESS OF A LAYER OF SILICON DAMAGED BY PLASMA ETCHING

TECHNICAL FIELD

The present invention relates to methods of investigating the effects of plasma treatments used in the manufacture of electronic devices on monocrystalline silicon and, more particularly, to a method of measuring the thickness of the surface layer of silicon altered by such a treatment.

BACKGROUND OF THE INVENTION

It is known that the plasma etching of a layer (of oxide or polycrystalline silicon, etc.) extending over the surface of a doped or non-doped monocrystalline silicon wafer may damage the surface of the monocrystalline silicon. This is due to the fact that the monocrystalline silicon remains exposed to the plasma during an over-etching stage which is necessary to ensure complete elimination of the layer. This surface damage of the silicon may cause a considerable deterioration in the electrical characteristics of the electronic devices produced by processing of the wafer. It is therefore important to investigate this phenomenon in order to try to reduce as far as possible the thickness of the damaged layer and its adverse effects on production output and on the reliability of the devices.

One of the most important mechanisms causing damage to the silicon is "amorphization" of the first layers of the monocrystalline silicon crystal lattice due to bombardment by the ionic species of the plasma. The extent of the damage depends substantially on the intrinsic characteristics of the etching equipment and on the process parameters selected on the equipment.

A need for suitable methods of evaluating new machines or process variations in real time or, in any case, within short periods of time has been felt for some time both by manufacturers and by users of plasma etching equipment.

Various methods are known for measuring the state of disorder of the monocrystalline silicon crystal lattice, such as, for example, those based on "helium ion channeling", on "Raman scattering", and on TEM (transmission electron microscopy) measurements. These methods provide accurate information on the thickness of the damaged layer but have the disadvantage of requiring expensive measurement equipment and very long response times (several days).

A method known as the "thermal wave" (TW) technique, which permits short response times (a few minutes) is also available. This is based on a measurement of the variations ($\Delta R$) in the reflectivity (R) induced by the thermoelastic deformation generated by a laser beam striking the surface of the silicon under test perpendicularly and measured by the deflection of a second laser beam. A measurement of $\Delta R/R$ provides a correlation, in arbitrary units, between the damage and the effects on the devices, but is fairly inaccurate because it depends upon the time elapsing between the etching and the measurement, on the crystal excitation frequency, and on temperature. Moreover, it cannot distinguish between the damaged silicon layer and the native oxide layer, that is, the layer of silicon dioxide which grows on the damaged silicon during exposure to air within the period of time between the completion of the plasma etching and the start of the measurement.

A method of measuring thicknesses with the use of an ellipsometer with a monochromatic light source is also known. The refractive index and the thickness of a layer which is transparent for the wavelength of the source can be obtained with this method. For an opaque layer, it is possible to obtain only the absorption coefficient (the imaginary portion of the refractive index), but not the thickness. This method can be used to measure a single layer on a larger substrate, that is, a substrate of a thickness much greater than the layer to be measured, such as a thin layer on a monocrystalline silicon wafer.

SUMMARY OF THE INVENTION

One object of the present invention is to provide a method of measuring the thickness of a surface layer of silicon damaged by plasma treatments.

A method of evaluating the effects of plasma damage is preferred to have the following characteristics:

fast measurement "feedback" (a short time should elapse between the etching and the production of the measurement results), sufficient sensitivity to detect significant thicknesses of damaged silicon layers, reproducibility of measurement results taken at different times, an ability to correlate the measurements made with the effects observed in the finished devices, low cost of the test equipment in comparison with that of the finished devices.

BRIEF DESCRIPTION OF THE DRAWINGS

The invention will be understood further from the following detailed description of an embodiment thereof given with reference to the appended drawings.

DETAILED DESCRIPTION OF THE INVENTION

Examples of a structure and a method for taking measurement according to the invention are described below.

A monocrystalline silicon wafer is preferably subjected to the same treatment to which a similar wafer intended for the manufacture of electronic devices is subjected. A layer to be etched with plasma, for example, a silicon dioxide layer, is deposited on the wafer. In one alternative embodiment, a further step is carried out to more closely reproduce the actual process conditions precisely, a photoresist mask is formed on the oxide layer. The wafer is then etched with the same equipment to be used for production wafers or for using test equipment and with the same parameters provided for during the etching of a wafer to be processed to produce actual devices. In particular, the duration of the over-etching will be the same as that provided for in the production process.

The photoresist is then removed by a standard method, for example, by a first dry removal step and a second wet removal step. This latter step is performed to remove a layer of fluorocarbon polymer which is usually deposited on the silicon surface which has undergone the over-etching.

Figure 1:
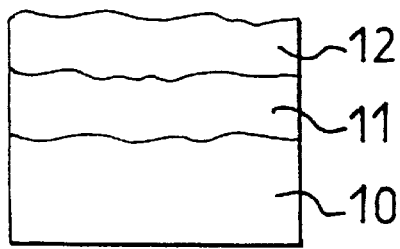
FIG. 1 shows, in section, the structure of a surface portion of a silicon wafer according to a model on which the method of the invention is based.
Figure 2:
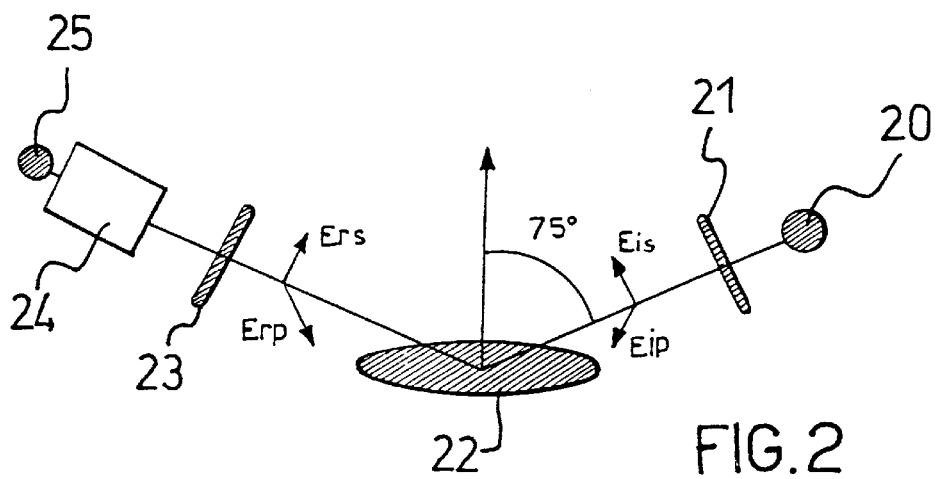
FIG. 2 shows schematically a measurement taken with a spectroscopic ellipsometer in order to implement a method according to the invention.

It is assumed that the surface structure of the silicon subjected to over-etching is similar to that shown in section in the model of FIG. 1: an intact monocrystalline silicon substrate 10, a damaged silicon layer 11, and a thin (2–3 nm) native silicon dioxide layer 12. This structure is subjected to measurement with a spectroscopic ellipsometer. This known device measures the variation of the state of polarization of a light beam after reflection on the surface of the sample containing the surface layer or layers to be measured. The schematic configuration of a spectroscopic ellipsometer is shown in FIG. 2. The light emitted by a white light source 20 (usually a xenon lamp which has a fairly continuous spectrum) is polarized linearly by a first polarizer 21. The polarizer is preferably rotated at constant speed. The light beam coming from the source strikes the wafer 22 with an angle of incidence usually selected to be close to the Brewster angle of silicon (75°), and is reflected from the silicon with a change in polarization state, that is, a change from linear polarization to elliptical polarization. The reflected light beam may be passed through a second polarizer 23 which is mounted in a fixed position (or which, in some devices, is oriented for each wavelength in order to achieve a favourable signal-noise ratio). The light signal then passes through a monochromator 24 in order finally to reach a detector 25.

The spectral range of the measurements is preferably between near UV (about 240 nm) and the near infra-red (about 900 nm).

The quantities measured are tan ($\psi$) and cos ($\Delta$) (or $\Delta$) which are linked with the incident electrical field Ei and with the reflected electrical field Er and with the optical properties of the sample by the following equation:

$$\rho = \frac{r_p}{r_s} = \tan(\Psi)e^{i\Delta}$$

in which $r_p$ and $r_s$ are reflection coefficients (complex) defined by the ratio between the incident electric field Ei and the reflected electric field Er in the directions parallel and perpendicular to the surface of the sample 22, respectively. A background technical discussion is provided in a publication by R. M. A. Azzam, N. M. Bashara, Ellipsometry and polarized light, North-Holland Publishing Company (1977), with particular reference to pages 269–277.

Figure 3:
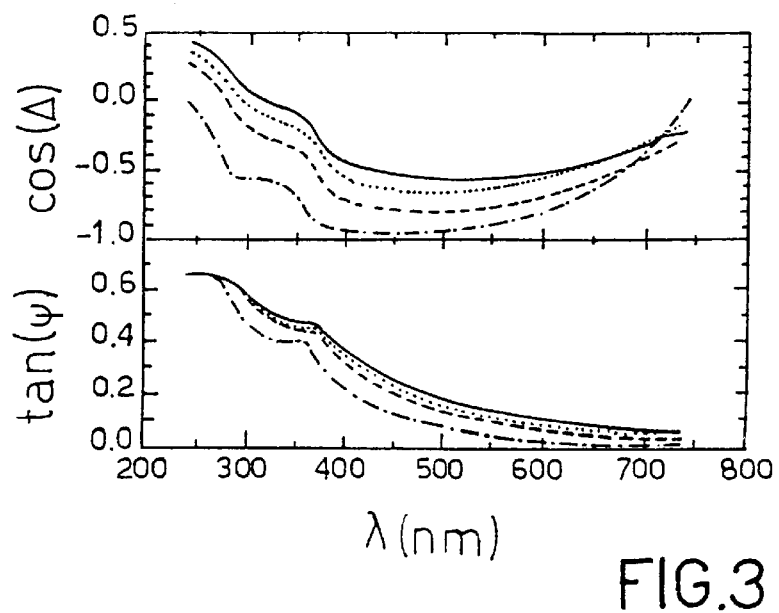
FIG. 3 is a graph showing how two ellipsometric quantities vary in dependence on the wavelength of the measurement light beam of a spectroscopic ellipsometer for different thicknesses of the altered silicon layer.

Experimental curves representing the ellipsometric quantities as functions of the wavelength $\lambda$ of the source are obtained from the values measured. FIG. 3 shows, for each of the two ellipsometric quantities, four experimental curves corresponding to four different thicknesses of the altered silicon layer 11 after plasma etching performed in different ways.

The ellipsometric quantities tan ($\psi$) and cos ($\Delta$) depend on the refractive index, on the absorption coefficient, and on the thickness of the layer under test, or of each superimposed layer of the sample under test if there is more than one layer. The theoretical curves of the ellipsometric quantities with variations of the wavelength of the source are calculated from a model of the sample under test by iteration of Fresnel equations. This calculation method is described, in the art, for example, in R. M. A. Azzam, N. M. Bashara, Elliposometry and polarized light, North-Holland Publishing Company (1977), with particular reference to pages 332–340.

The refractive indices and absorption coefficients of the respective layers are inserted in the Fresnel equations as known parameters. The refractive index of monocrystalline silicon and of silicon dioxide are known but the optical characteristics of the damaged silicon layer are not. According to a preferred embodiment of the method of the invention, the hypothesis is made that the damaged layer is described optically as a combination of amorphous silicon and polycrystalline silicon, two materials the refractive indices of which are known. The actual refractive index of the damaged layer is thus calculated by means of Bruggeman's "effective mean equation" (EMA):

$$f\frac{\varepsilon_a - \varepsilon}{\varepsilon_a + 2\varepsilon} + (1-f)\frac{\varepsilon_p - \varepsilon}{\varepsilon_p + 2\varepsilon} = 0$$

in which $\epsilon_a$ is the dielectric function of the first component, in this case the amorphous silicon, $\epsilon_p$ is that of the second component, that is, the polycrystalline silicon, and $\epsilon$ is the effective dielectric function of the combination. The quantity f is a coefficient which defines the weight of the first component relative to the second in the description of the optical properties of the damaged silicon.

Details of the EMA equation and its applications can be obtained from the publication D. E. Aspnes, Thin Solid Films 89, 249 (1982).

The theoretical curves thus define the ellipsometric quantities in dependence on the wavelength of the light source and on three unknown parameters: the thickness of the damaged silicon layer, the thickness of the native oxide layer, and the coefficient f.

The experimental and theoretical curves are then compared by means of a "fitting" procedure, for example, the Levenberg-Marquard procedure, which is similar to the least squares method based on the minimization of the deviations with variations of the unknown parameters. This method, which is described, for example, in Press et al., Numerical recipes in C, The art of scientific computing, Cambridge University Press, New York (1988), can determine which values of these three unknowns render the theoretical and experimental curves superimposable within a given tolerance band.

Figure 4:
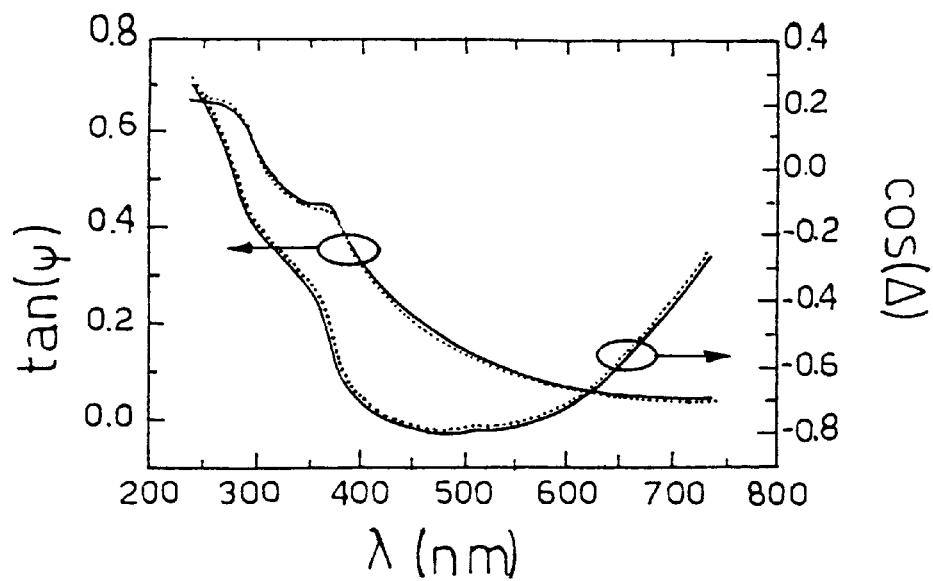
FIG. 4 is a graph showing the theoretical and experimental curves of two ellipsometric quantities as functions of the wavelength.

FIG. 4 shows, by way of example, the experimental curves (dotted lines) of the two ellipsometric measured quantities tan ($\psi$) and cos ($\Delta$) as functions of the wavelengths $\lambda$, associated, after a fitting procedure, with the corresponding theoretical curves (continuous lines). In one example, the values determined for the unknowns are: the thickness of the native oxide layer: 5.1 nm, the thickness of the altered silicon layer: 5.4 nm, and the proportion of amorphous silicon (coefficient f): 62%.

The measurements can be taken for any silicon wafer using this technique. The measurement can also be made over the entire surface of the silicon wafer in order to obtain a map of the damaged silicon thickness values. This measurement operation can be performed by the structure and method according to the invention for a silicon wafer within time range on the order of one minute.

Figure 5:
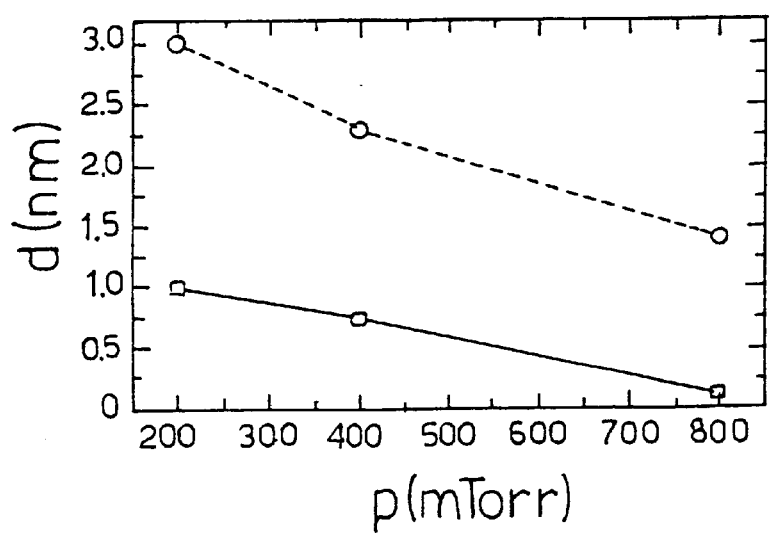
FIG. 5 is a graph which shows the variation of the thickness of a damaged silicon layer in dependence on a parameter of the plasma etching process.

If using wafers subjected to etching in different operative conditions are available, it is possible to produce graphs in which the thickness of the damaged layer is related to a process parameter. For example, in FIG. 5, the variation of the thickness d is shown as a function of the pressure p present in the reactor used for the plasma etching for two different powers.

The results can be reported thus very quickly. It can be determined if the quality is within an acceptable range. If analysis of the damage caused by different process steps is desired, it is possible to vary one or more selected process parameters and then perform the measurement on each variation. According to one embodiment, a plurality of wafers can be processed using variations in some parameters and then each tested. A preferred set of process parameters can then be selected which causes the least damage.

The method according to the invention has also been found to be very accurate for measuring two or more superimposed layers and to have high sensitivity (0.1 nm).

From the foregoing it will be appreciated that, although specific embodiments of the invention have been described herein for purposes of illustration, various modifications may be made without deviating from the spirit and scope of the invention. Accordingly, the invention is not limited except as by the appended claims.

Other reflection and measurement equipment can be used to measure the optical qualities of the silicon stack as shown in FIG. 1, and the results used to determine the thickness of the altered silicon layer.

What is claimed is:

1. A method of measuring the characteristics of a surface of a monocrystalline silicon wafer subjected to plasma etching, the surface having silicon altered as a result of the plasma etching and being covered by a thin layer of silicon dioxide, the method comprising:

measuring, with a spectroscopic ellipsometer, the values of two quantities that are dependent on the thickness of the altered silicon and of the thin silicon dioxide layer with variations in the wavelength of the light of the measurement beam of the ellipsometer, obtaining from these measured values respective experimental curves representing the two quantities as functions of the wavelength, calculating the theoretical curves of the two quantities as functions of the wavelength considering the refractive indices and absorption coefficients of silicon dioxide and of the altered silicon as known parameters and the thickness of the altered silicon layer and the thickness of the thin silicon dioxide layer as unknowns, obtaining the refractive index of the altered silicon by considering the altered silicon as a combination of amorphous silicon and polycrystalline silicon, and in which, during the calculation of the theoretical curves, the proportion (f) of amorphous silicon and of polycrystalline silicon is also considered as unknown, comparing the theoretical curves with the respective experimental curves in order to determine for which values of the unknowns the curves under comparison approximate to one another the best, and extracting from the values determined the value that relates to the thickness of the altered silicon.

2. The method according to claim 1, in which the refractive index of the altered silicon is calculated by means of Bruggeman's effective mean equation (EMA).

3. The method according to claim 1, in which the theoretical curves of the two quantities are calculated with the use of Fresnel equations.

4. The method according to claim 1, in which the theoretical curves and the experimental curves are compared with the use of the Levenberg-Marquard method.

5. A method of estimating the thickness of altered silicon in the surface of monocrystalline silicon comprising:

obtaining and storing reference data regarding two quantities related to the optical characteristics of altered silicon, including obtaining the refractive index of the altered silicon by considering the altered silicon as a combination of amorphous silicon and polycrystalline silicon, and in which, during the calculation of the theoretical curves, the proportion (f) of amorphous silicon and of polycrystalline silicon is also considered as unknown, measuring the optical values of the two quantities that are dependent on the thickness of the altered silicon;

comparing the measured values to the reference data previously stored that relate the two quantities to the thickness of the altered silicon; and outputting from the comparison between the measured values and the reference data the thickness of the altered silicon.

6. The method according to claim 5 further including:

measuring a third quantity of a plurality of reference layer; and storing the measured values to create a reference data set.

7. The method according to claim 5 further including:

processing a plurality of silicon wafers under different respective process parameters;

measuring the values of two quantities that are dependent on the thickness of the altered silicon on each respective wafer;

comparing the measured values to the reference data previously stored that relate the two quantities to the thicknesses of the altered silicon for each respective wafer;

outputting from the comparisons between the measured values and the reference data the thickness of the altered silicon for each respective wafer; and selecting a set of process parameters that provide the lower thickness of the altered silicon than other process parameters with the different respective processes.

* * * * *